(12) United States Patent
Sabri

(10) Patent No.: US 7,490,602 B2
(45) Date of Patent: Feb. 17, 2009

(54) STOMACH BELT FOR WEIGHT LOSS

(76) Inventor: Mahmoud Talaat Sabri, 57 Meadow La., Danville, PA (US) 17821

( * ) Notice: Subject to any disclaimer, the term of this patent is extended or adjusted under 35 U.S.C. 154(b) by 405 days.

(21) Appl. No.: 11/243,301

(22) Filed: Oct. 3, 2005

(65) Prior Publication Data
US 2007/0078296 A1   Apr. 5, 2007

(51) Int. Cl.
*A61F 5/24* (2006.01)
*A61F 5/28* (2006.01)
*A61F 5/00* (2006.01)

(52) U.S. Cl. .................. 128/96.1; 128/99.1; 128/102.1; 128/106.1; 128/115.1; 602/13

(58) Field of Classification Search ............... 128/96.1, 128/95.1, 99.1, 100.1, 102.1, 106.1, 115.1; 602/5, 6, 13; 606/201
See application file for complete search history.

(56) References Cited

U.S. PATENT DOCUMENTS

| | | | |
|---|---|---|---|
| 4,133,315 A | 1/1979 | Berman et al. | |
| 4,246,893 A | 1/1981 | Berson | |
| 4,485,805 A | 12/1984 | Foster, Jr. | |
| 4,694,827 A | 9/1987 | Weiner et al. | |
| 5,259,399 A | 11/1993 | Brown | |
| 5,666,104 A | 9/1997 | Pollack et al. | |
| 5,797,851 A * | 8/1998 | Byrd | 600/499 |
| 5,823,913 A * | 10/1998 | Aruin et al. | 482/4 |
| 5,843,008 A * | 12/1998 | Gerhard | 602/5 |
| 5,993,473 A | 11/1999 | Chan et al. | |
| 6,558,400 B2 | 5/2003 | Deem et al. | |
| 6,579,301 B1 | 6/2003 | Bales et al. | |
| 6,881,179 B2 | 4/2005 | Mostardi | |
| 2003/0208113 A1 | 11/2003 | Mault et al. | |
| 2005/0004436 A1 | 1/2005 | Nissila et al. | |

* cited by examiner

*Primary Examiner*—P Bianco
(74) *Attorney, Agent, or Firm*—McHale & Slavin, P.A.

(57) ABSTRACT

An apparatus and method for treating obesity comprising an inflatable balloon attached to an inner portion of a belt. The belt is wrapped around an individual's abdomen in the vicinity of the stomach. The balloon is inflated prior to consuming a meal and left in place for a certain period of time. The apparatus is then removed from the individual's abdomen.

15 Claims, 2 Drawing Sheets

STOMACH BELT FOR WEIGHT LOSS

FIELD OF THE INVENTION

The present invention relates to a device which can be used by the average person to help control the amount of food that they consume. This aids in the prevention and management of obesity by preventing and decreasing excessive food consumption.

BACKGROUND OF THE INVENTION

Obesity has become a major health problem in the United States and worldwide. In the United States alone, it has been estimated that obesity accounts for more health care expenditures than any other health condition, including smoking. Obesity has been linked to high blood pressure which leads to hypertension, high levels of blood glucose associated with diabetes, high concentrations of blood cholesterol and triglycerides which are associated with cardiovascular disease, certain types of cancer, increased stress on weight-bearing joints which can lead to arthritis, depression, sleep apnea and gall bladder disease. Many solutions to achieve weight loss for the treatment of obesity have been proposed. They can be summarized and placed into four different categories. Physical exercise, dietary restrictions, pharmaceuticals and surgery.

An substantial increase in physical exercise has long been recognized as a method of preventing weight gain. Vigorous exercise is normally recommended since this results in a substantial increase in the energy expended by a person. Whenever there is more energy expended than taken in through the consumption of food, weight loss occurs. This solution has been proposed by physicians and those persons in the health care area for many years. When exercise is performed on a regular basis an additional benefit is realized. This regular exercise increases the body's rate of metabolism. An increase in the rate of metabolism will result in more energy being expended even when a person is resting. This is still the preferred solution today. However, many individuals do not have the time or stamina to do these vigorous exercises on a routine basis. In addition, the morbidly obese individuals risk further damage to their health, for example by heart attacks, from such exercise.

Another solution involves dietary restrictions. This involves eating the "right" kinds of foods, for example those which have a low fat and sugar content. There are many food available today which are considered to be "diet" versions of popular foods. The most popular of these is diet soda in which a chemical, such as Saccharin, is substituted for the sugar. The chemical does not have any calories therefore the person drinking the soda will not consume any calories. Also the amount of food consumed should be limited. A healthy body will give an indication that the person has consumed enough food and is "full". If this signal is ignored, the individual tends to expand the stomach, Ghrelin will be secreted by the stomach as a result of it being distended. Ghrelin in turn stimulates the secretion of Agoti-related protein (Agrp) and Neuropeptide Y (Npy) within the hypothalamus thereby stimulate food intake. The size of food portions in the marketplace, including restaurants, has progressively increased which has resulted in the consumer ignoring the "full" indicator and eating all the food that has been purchased.

Another solution involves the use of pharmaceuticals such as stimulative or appetite suppressive drugs. While this may be a satisfactory solution for many, the use of pharmaceuticals in the treatment of obesity is not without drawbacks. For example, individuals using such drugs are at risk of becoming addicted or ill-affected by the side effects of the drugs. Further, these drugs oftentimes become less effective over time due to the development of drug tolerances by the body.

Surgical solutions to the obesity problem have also been proposed. These involve reducing the volume of the gastric cavity by creating a small pouch gastric bypass, such as a Laparoscopic gastric bypass and a Roux-en-Y gastric bypass. Another method of reducing the volume of the gastric cavity involves surgically placing a balloon or inflatable bladder adjacent to or into the stomach and inflating the balloon. This enables the person to feel "full" after consuming a relatively small portion of food. A number of gastric balloon systems have been proposed. In one type of system the balloon is inserted into the stomach and inflated to a specific volume. The volume of the balloon remains constant over the time period that the balloon is employed to cause a weight loss. A drawback to this has been observed. In many cases the stomach expands to accommodate the balloon and recovers a portion or all of its former capacity for food intake, thereby defeating the purpose of the balloon and reducing the effectiveness of the treatment.

Another type of gastric balloon system permits the volume of the gastric balloon to be varied. The purpose of changing the volume of the balloon is to provide periods of feelings of relief and well-being to the patient. One system, disclosed in U.S. Pat. No. 4,133,315 to Berman, utilizes a filling/release tube coupled to the balloon and which in one embodiment extends surgically through the stomach wall and through the wall of the abdomen. Fluid can be pressurized into the balloon through the tube to cause the balloon to expand, or it can be released/evacuated from the tube to permit the balloon to collapse, thereby varying the volume of the balloon.

DESCRIPTION OF THE PRIOR ART

U.S. Pat. No. 4,246,893 to Berson discloses a method and device for treating obesity in human patients. A balloon is inserted in a person's abdomen and placed adjacent to and anterior of the stomach. After it is in place it is filled with a suitable fluid through filling tube 3 and adjusting port 4. The device remains inside the patient for a substantial period of time. This device requires surgery to be performed for the device to be correctly located and is not readily reversible.

U.S. Pat. No. 6,579,301 to Bales et al. discloses a device which is located entirely within the stomach. A pump transfers a fluid from a reservoir to a bladder. The bladder expands and contracts depending on the amount of fluid it contains. This expansion and contraction is used during the treatment period to limit the amount of food taken in. Also, the contraction is utilized to relieve patient discomfort. The system can be operated using sensors in the body or from a remote control device located exteriorly of the patient. This device also requires surgery to be performed and is not readily reversible.

U.S. Pat. No. 5,666,104 to Pollack et al. disclose another approach utilizing a monitor. A belt, including a sensor and an alarm is worn by the patient. After the patient has consumed too much food their waist size increases. This expands the belt and activates the alarm. The sensor includes a delay circuit to prevent activation of the alarm because of short, temporary expansions of the waist. The alarm in this device operates only after the patient has consumed too much food.

None of these devices can be used for only a short period of time, such as mealtime or whenever food is consumed. Also, the instant invention does not require that surgery, and the risks associated therewith, be performed.

SUMMARY OF THE INVENTION

The present invention is directed to a device which can be adjustably positioned about the waist of an individual, so as to position an inflatable element in juxtaposition to the individual's stomach, whereupon inflation of the element causes pressure to be applied to the individual's stomach, thereby creating a sense of fullness or satiety, effective to reduce the individual's overall food consumption. In an illustrative, albeit a non-limiting embodiment, the device is in the form of a belt which is worn by a user to help control the amount of food consumed. The belt contains a bladder positioned on the interior side thereof which can be inflated or deflated by the user.

Accordingly, it is a primary objective of the instant invention to provide a device which can be used by an individual without the assistance of a doctor, specialized training, or the need for surgery, which is effective to reduce food consumption.

It is a further objective of the instant invention to provide a device to help in weight loss which only need be employed when a person is consuming food and for a short period thereafter.

It is yet another objective of the instant invention to provide a device to help in weight loss which is adjustable by the person using the device and does not require professional assistance or special training.

It is a still further objective of the invention to provide a weight loss device for initiating a sense of satisfaction or fullness while eating, wherein the device is readily adjustable by the user to provide varying degrees of pressure as may be desired or advisable.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
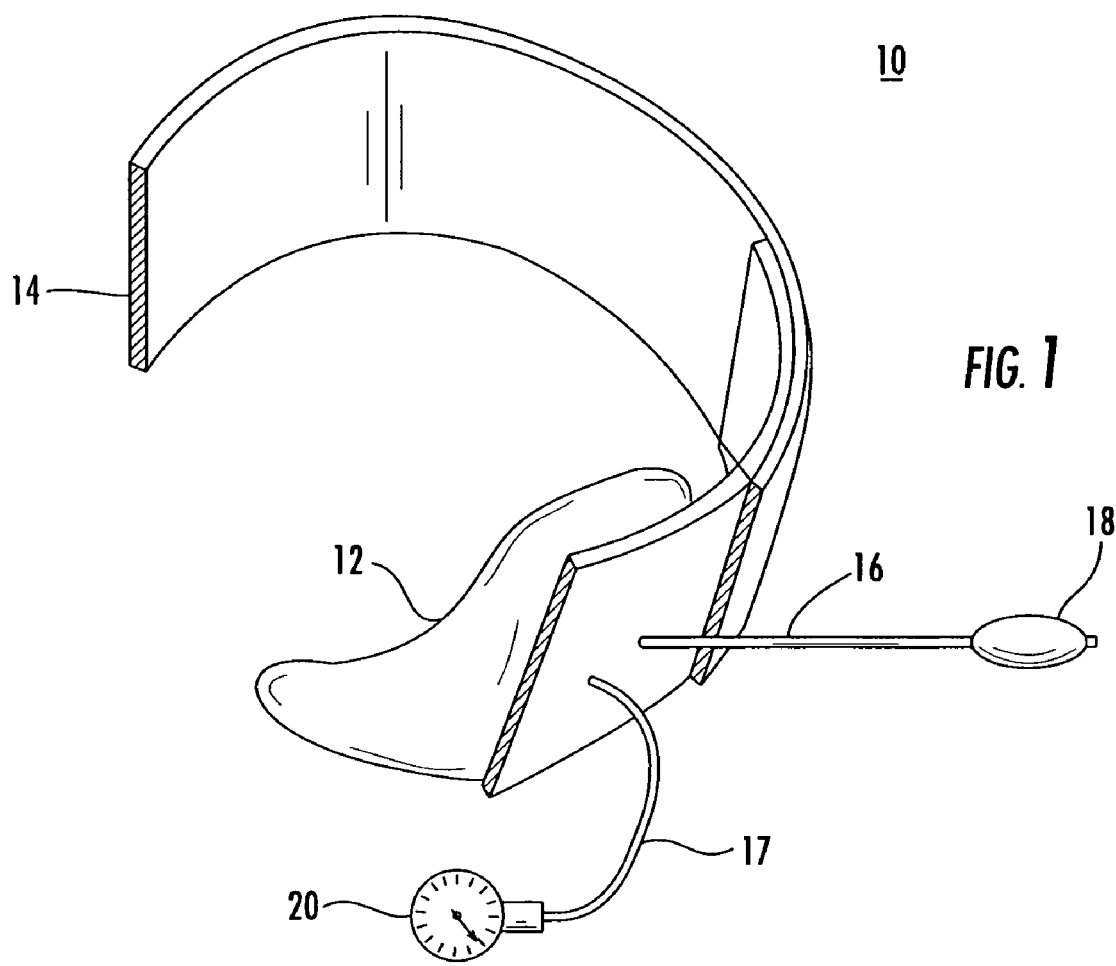
FIG. 1 is a perspective view, with a portion cut away, of the weight loss device wherein the bladder is illustrated as being inflated.
Figure 2:
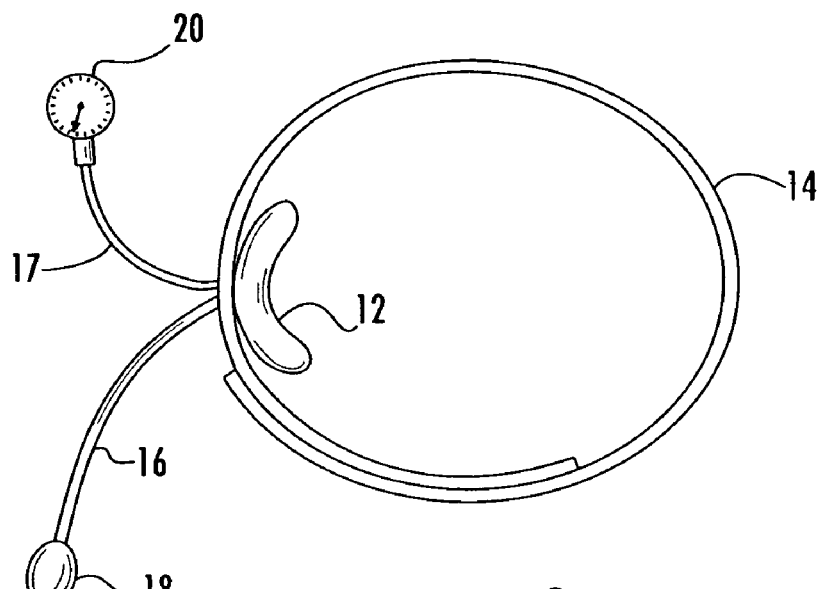
FIG. 2 is a top view of the weight loss device, looking downward, wherein the bladder illustrated as being deflated.
Figure 3:
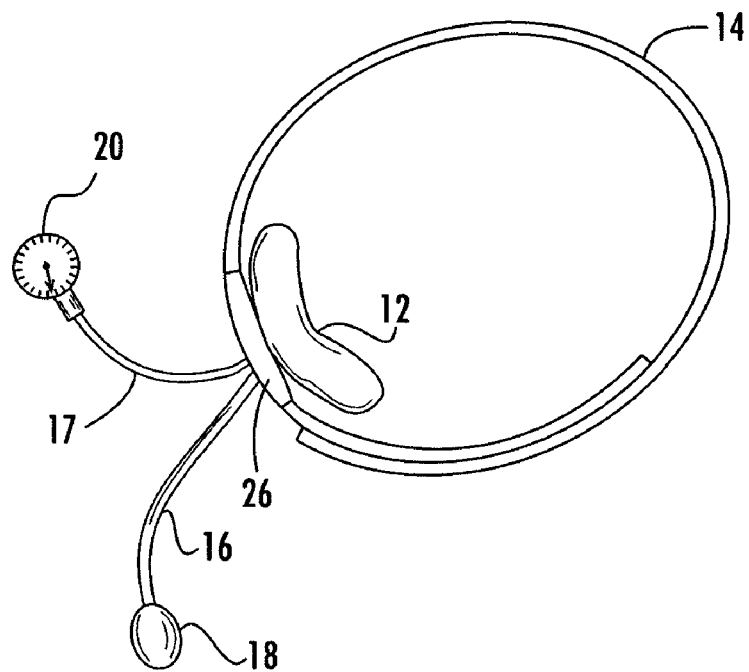
FIG. 3 is a top view of the weight loss device looking downward illustrating an alternative embodiment of the device.
Figure 4:
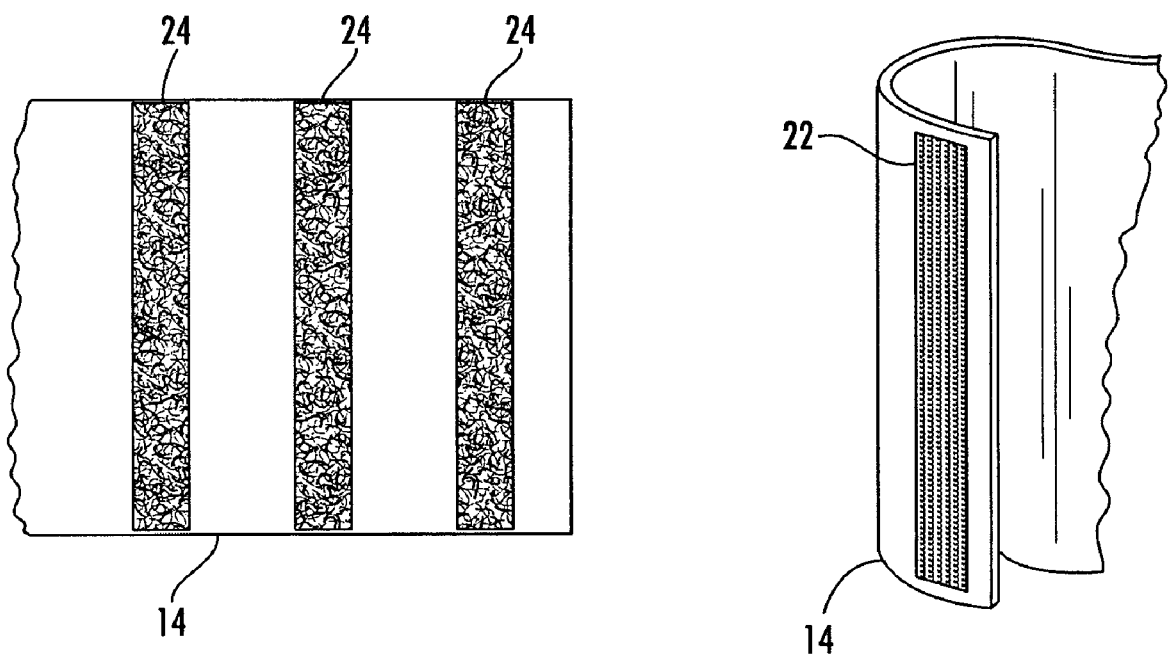
FIG. 4 is a partial frontal elevational view of the end portions of the weight loss device.

In a preferred albeit non-limiting embodiment of the invention as shown in FIG. 1 the device 10 comprises an inflatable balloon or bladder 12. The bladder 12 is preferably formed as a flexible walled, imperforate, air inflatable member which is located on the inside portion of a belt or securement means 14. The balloon is made from a non-latex rubber or similar material. One end of a tube or hose 16 is connected or fluidly coupled to the balloon 12. The other end of the tube is connected or fluidly coupled to a source of pressured air such as a hand pump 18 or a mechanical/electrical pump. A gauge 20 may also be connected or fluidly coupled to the balloon via a tube or hose 17 to measure the pressure inside of the balloon. The belt or securement means 14 is formed from an elongate, flexible sheet material. One suitable sheet material is nylon, but other flexible materials could be used. Preferably the belt is formed from multiple layers or plies, but a single ply may be employed. As shown in FIG. 4, the belt 14 includes fasteners 22 located along one end portion of the belt which cooperate with fasteners 24 positioned at varying distances along the length of the outer surface of the belt. These positions are selected so as to allow the belt to be positioned around an individual's abdomen in a snug relationship prior to inflation of the balloon. The preferred fastener is a hook and loop fastener, such as VELCRO®. Other equivalent fasteners may also be employed such as snaps, buttons, buckles, zippers, etc. As shown in FIG. 3, a rigid piece of material 26, preferably but not limited to hard plastic, is positioned on the interior portion of the belt adjacent the balloon. This provides a rigid surface against which the balloon can push upon inflation so as to enable it to push against the stomach and compress it. When the belt is formed from multiple layers of material, the rigid piece of material may be located on the inside surface of the belt, in between the layers of material which form the belt.

The position of the balloon in relation to a person's stomach must first be determined. Once this is determined, the belt is placed around an individual's upper abdomen with the balloon adjacent anatomically to the stomach. Then the balloon is inflated. The inflation pressure is 350-400 mmHg depending on the size and comfort level of the individual.

The individual will normally next consume the recommended amount of water which is normally 1 glass or approximately 8 ounces. This is normally done 10-15 minutes before consuming a meal. The meal is then consumed. The stomach will now normally distend and then contract so as to empty its contents into the small intestine. This usually occurs in less than 10 minutes. The individual can remove the belt about 10-15 minutes after he has a feeling of fullness or satiety. Once the stomach has contracted, it will not fully distend until the next meal so that an individual will not have the desire to consume more food.

In addition to using the belt for meals it should also be used when snacks are eaten or any food or drink is consumed. It is preferably not to snack in between meals, but if a person feels compelled to do so they should employ the belt.

The belt is normally manufactured in three sizes small, medium and large. These along with the individual adjustability of each belt provide a range of sizes to accommodate almost everyone. For individuals requiring special sizes, not normally manufactured, custom made belts can be made to order.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An external abdominal pressurization assembly useful for reducing food consumption in an individual comprising:
   securement means for adjustably securing said assembly about an abdominal region of said individual;
   an inflatable element constructed and arranged for adjustable engagement with said securement means, wherein said inflatable element is positioned in juxtaposed relation to an individual's stomach cavity;
   said securement means including a rigid member positioned between said inflatable element and an outer portion of said securement means; and
   pressurizing means fluidly coupled with said inflatable element for reversibly pressurizing said inflatable element;
   whereby pressure is controllably applied to the individual's stomach cavity from said inflatable element sufficient to reduce food consumption by said individual.

2. The external abdominal pressurization assembly of claim 1 wherein said inflatable element comprises a flexible-walled, imperforate, air-inflatable member.

3. The external abdominal pressurization assembly of claim 2 wherein said flexible-walled, imperforate, air-inflatable member includes wall portions which conform to the shape of said individual's stomach cavity upon inflation.

4. The external abdominal pressurization assembly of claim 3 wherein said pressurizing means comprises a means for providing a pressurized air source, and means for fluidly coupling said pressurized air source to said inflatable member;
   wherein upon inflation said inflatable member applies pressure to said individual's stomach cavity.

5. The external abdominal pressurization assembly of claim 4 wherein said pressurizing means further comprises a pump fluidly coupled to said air-inflatable member whereby said inflatable member is pressurized to a desired pressure or dimension.

6. The external abdominal pressurization assembly of claim 1 wherein said securement means is a body member fabricated of flexible sheet material constructed and arranged to fit around an abdomen of a person.

7. The external abdominal pressurization assembly of claim 6 wherein said flexible sheet comprises an elongate sheet, said elongate sheet having first and second end portions and first and second surfaces, said first surface is juxtaposed to the abdominal region of said individual when said elongate sheet is received around said individual and means to releasably attach said inflatable element to said first surface.

8. The external abdominal pressurization assembly of claim 7 including fastening means constructed and arranged to attach one of said first and second end portions to said second surface.

9. The external abdominal pressurization assembly of claim 8 wherein said fastening means comprises a hook and loop fastener.

10. The external abdominal pressurization assembly of claim 8 wherein the fastening means comprises snaps.

11. The external abdominal pressurization assembly of claim 8 wherein the fastening means comprises a zipper.

12. An external abdominal pressurization assembly useful for reducing food consumption in an individual comprising:
    securement means for adjustably securing said assembly about an abdominal region of said individual;
    an inflatable element constructed and arranged for adjustable engagement with said securement means, said inflatable element is positioned in juxtaposed relation to said individual's stomach cavity;
    pressurizing means fluidly coupled with said inflatable element for reversibly pressurizing said inflatable element, said pressurizing means comprises a pump;
    said securement means comprises an elongate sheet of flexible sheet material, said elongate sheet has first and second end portions and first and second surfaces, said first surface positioned in juxtaposed relation to and surrounding said individual's abdomen;
    said securement means including a rigid member positioned between said inflatable element and said second surface of said elongate sheet;
    said inflatable element comprising a flexible-walled, imperforate, air-inflatable member including plural wall portions which conform to the shape of said individual's stomach cavity upon inflation;
    fastening means constructed and arranged to attach one of said first and second end portions to said second surface;
    whereby pressure is controllably applied to said individual's stomach cavity from said inflatable element sufficient to reduce food consumption by said individual.

13. The external abdominal pressurization assembly of claim 12 wherein said fastening means comprises a hook and loop fastener.

14. The external abdominal pressurization assembly of claim 12 wherein the fastening means comprises snaps.

15. The external abdominal pressurization assembly of claim 12 wherein the fastening means comprises a zipper.

* * * * *